United States Patent [19]

Eckstein

[11] Patent Number: 4,629,335

[45] Date of Patent: Dec. 16, 1986

[54] INDICATOR TUBE COMBINED WITH A TEMPERATURE GAUGE

[75] Inventor: Wolfgang Eckstein, Sereetz, Fed. Rep. of Germany

[73] Assignee: Drägerwerk Aktiengesellschaft, Fed. Rep. of Germany

[21] Appl. No.: 475,477

[22] Filed: Mar. 15, 1983

[30] Foreign Application Priority Data

May 12, 1982 [DE] Fed. Rep. of Germany ....... 3217832

[51] Int. Cl.$^4$ .............................................. G01K 3/00
[52] U.S. Cl. .................................... 374/142; 116/206; 116/207; 422/86; 422/87
[58] Field of Search ....................... 374/142, 162, 148; 116/206, 207; 422/86, 87

[56] References Cited

U.S. PATENT DOCUMENTS 2,648,976  8/1953  Bur ...................................... 374/142
3,651,695  3/1972  Brown ................................. 374/147
3,955,420  5/1976  Parker ................................. 116/207
4,230,457  10/1980 Leichnitz ............................. 422/86
4,389,372  6/1983  Lalin ................................... 422/86

FOREIGN PATENT DOCUMENTS 2709632  7/1978  Fed. Rep. of Germany ........ 422/86
2037982  7/1980  United Kingdom .................. 422/86

Primary Examiner—Charles Frankfort
Assistant Examiner—Denis E. Corr
Attorney, Agent, or Firm—McGlew and Tuttle

[57] ABSTRACT

An indicating tube for detecting gas type and characteristics comprises a hollow transparent tube having a passage therethrough for the passage of a gas to be detected and with a first material in the passage giving a visual indication of the gas characteristic and a second material in the passage which gives a visual indication of the temperature characteristic of the gas.

3 Claims, 2 Drawing Figures

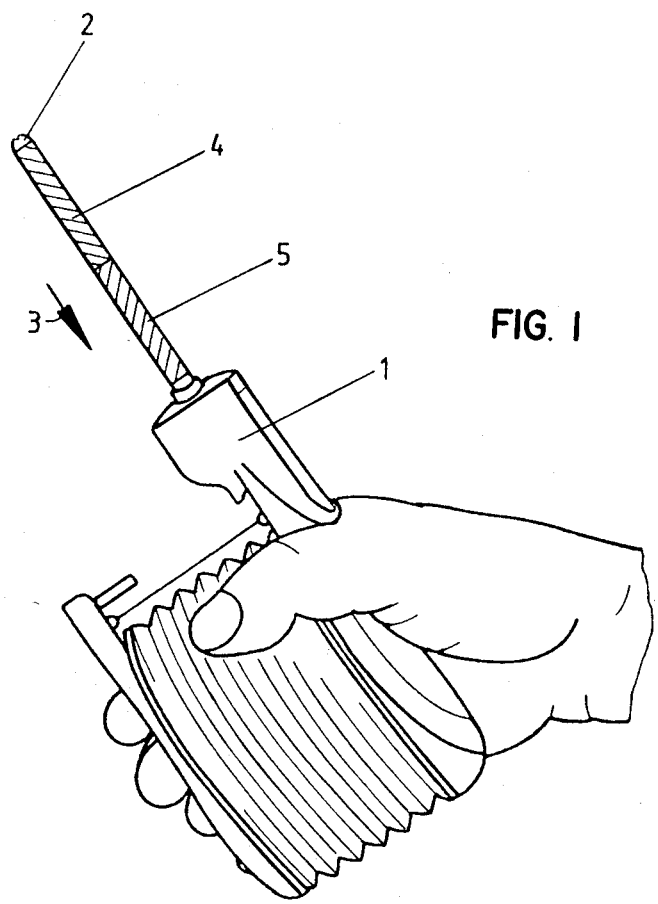
FIG. 1
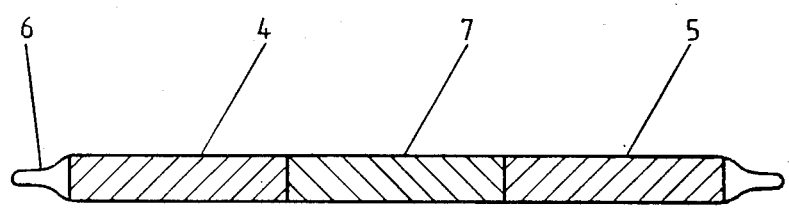
FIG. 2
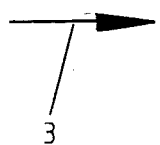

INDICATOR TUBE COMBINED WITH A TEMPERATURE GAUGE

FIELD AND BACKGROUND OF THE INVENTION

This invention relates in general to gas detection devices and in particular to a new and useful device comprising an indicator tube for a gas having a temperature indicator for the gas.

Time and again, a prior art indicator tube is to be applied in instances where, in addition to measuring extraneous gases in air or other gases, the temperature of the carrier gas is to be determined, for example while measuring the efficiency of fireplaces or also to be able to take into account the possible impact of the temperature on the measurement itself. The temperature of the carrier gas may, of course, be measured at the sampling location or in advance by means of well known temperature measuring equipment based on a physical principle; however, this is relatively complicated since two measuring devices must separately be employed, one for measuring the temperature and one for measuring the extraneous gas.

A prior art device for measuring the waste gases comprises a probe tube for taking the waste gas off by suction. The probe tube accommodates wires leading from a thermocouple which is secured to the tip under a guard. The rear end of the probe carries connections for a $CO_2$ analyzer and for a temperature indicator. To effect the measuring operation, the probe tube is introduced into the waste gas conduit through a check hole. Then, the waste gas sample is taken off by the $CO_2$ analyzer and analyzed. At the same time, the temperature of the waste gas is measured through the thermal couple and a temperature indicator.

This prior art equipment in fact requires two measuring devices, is expensive in instrumentation and maintenance, and cannot be used on occasions of instantaneous need, since is is complicated. It is hardly suitable for spot checks (German utility model No. 79 29 123).

SUMMARY OF THE INVENTION

The invention is directed to a device in which a gas indicator tube is combined with a temperature gauge and with which the temperature of the checked gas can be measured simultaneously with the extraneous gas presence or proportion.

Many years of experience have shown the necessity for having means for effecting both a gas and temperature measurement. A single, known and simple measuring operation is needed for both measurements. The indication is obtained promptly and can be read directly at adjacent locations and documented by the used indicator tube itself.

In one embodiment, the indicator tube further accommodates a cooling layer between the temperature measuring and the gas measuring layers, and is then usable also at extremely high temperatures.

Accordingly, it is an object of the invention to provide a detector which includes means for indicating the temperature of the gas as well as the characteristic thereof.

A further object of the invention is to provide a gas detecting tube which comprises a glass tube having ends which are breakable at each end and which includes a layer of a material for indicating a characteristic of the gas or the type of gas which is passed therethrough as well as its temperature and advantageously also has means for changing the temperature, for example cooling it.

A further object of the invention is to provide a gas indicating tube which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a perspective view of an indicator tube being used to sample gas constructed in accordance with the invention; and FIG. 2 is an elevational view of an indicator tube of another embodiment of the invention.

DESCRIPTION OF THE PREFERRED EMBODIMENTS

Referring to the drawings in particular the invention embodied therein in FIG. 1 comprises an indicator tube 2 which advantageously is transparent and hollow and has a passage therethrough for the passage of a gas to be detected in a direction of the arrow 3. In the passage, there are first means designated 5 giving visual indication of a gas characteristic and second means 4 in the passage which give a visual indication of a temperature characteristic of the gas. Th first means 5 comprises a gas measuring layer and the second means 4 comprises a temperature measuring layer and in the normal arrangement the temperature measuring layer would precede the gas measuring layer.

By means of a well known bellows pump 1, a gas to be checked is taken by suction through an inventive indicator tube 2 equipped for simultaneously measuring the temperature. The gas flows therethrough in the direction 3. The gas passes first through the temperature measuring layer 4 and then through the gas measuring layer 5.

Temperature measuring layer 4 is responsive either by completely changing color in a known manner, or by changing color to a definite length which is then the measure of the gas temperature. Suitable graduations on the glass tube 2 may indicate the temperature directly for color length temperature changes.

The inventive arrangement provides an arrangement wherein the temperature is ordinarily indicated in the temperature measuring layer 4 either by a color change or by the length of coloration read on a scale which is imprinted on the glass tube 2. For special cases where a high temperature gas is to be tested, the cooling layer 7 is employed between the temperature measuring layer and the gas measuring layer and this layer acts to cool the gas as is passes through before it is directed to the detection layer 5.

While specific embodiments of the invention have been shown and described in detail to illustrate the application of the principles of the invention, it will be understood that the invention may be embodied otherwise without departing from such principles.

What is claimed is:

1. An indicator device comprising a hollow transparent gas indicator tube having breakable ends which are breakable for the flow of a gas through said tube in a gas flow direction, a temperature measuring layer within said tube through which said flow passes and which changes color in accordance with temperature variations of said gas, a gas measuring layer adjacent said temperature-measuring layer giving an indication of another property of said gas arranged in said tube after said temperature measuring layer in the gas flow direction through which said gas flow passes said temperature- measuring layer providing an indication of the temperature of the gas to be measured by said gas-measuring layer, said indications being displayed at directly adjacent locations on said tube.

2. An indicator device according to claim 1, wherein said temperature measuring layer includes means varying in color along its length in accordance with the temperature of the gas passing therethrough.

3. A device according to claim 1, including a cooling layer in said tube located between said gas measuring layer and said temperature measuring layer.